United States Patent [19]

Dauth et al.

[11] Patent Number: 5,426,200
[45] Date of Patent: Jun. 20, 1995

[54] ORGANOSILOXANE-BONDED TRANSITION METAL COMPLEXES

[75] Inventors: Jochen Dauth; Udo Peetz; Bernward Deubzer, all of Burghausen, Germany

[73] Assignee: Wacker-Chemie GmbH, Munich, Germany

[21] Appl. No.: 276,921

[22] Filed: Jul. 19, 1994

[30] Foreign Application Priority Data

Jul. 22, 1993 [DE] Germany .................. 43 24 685.0

[51] Int. Cl.⁶ .................. C07F 7/08; C07F 7/10
[52] U.S. Cl. .................. 556/9; 556/12; 528/15; 546/14; 546/4; 546/12; 549/4; 549/214; 534/551; 534/552
[58] Field of Search .................. 556/9, 12; 528/15; 546/14, 406; 549/4, 214

[56] References Cited

U.S. PATENT DOCUMENTS

| | | | |
|---|---|---|---|
| 2,476,166 | 7/1949 | Wayo . | |
| 3,445,420 | 5/1969 | Kookootsedes et al. . | |
| 4,504,645 | 3/1985 | Melancon . | |
| 5,175,325 | 12/1992 | Brown et al. . | |
| 5,185,458 | 2/1993 | Huggins | 556/9 |
| 5,187,134 | 2/1993 | Panster et al. . | |
| 5,312,937 | 5/1994 | Waier et al. | 556/9 |
| 5,318,935 | 6/1994 | Canich et al. | 556/12 X |
| 5,354,831 | 10/1994 | Panster et al. | 556/9 X |

FOREIGN PATENT DOCUMENTS

| | | |
|---|---|---|
| 2111643 | 6/1994 | Canada . |
| 0602638 | 6/1994 | European Pat. Off. . |

OTHER PUBLICATIONS

D. S. Moore et al., Advances in Inorganic Chemistry and Radiochemistry, vol. 30, pp. 1–68, 1986.
Tandon et al., Synth. React. Inorg. met.-Org. Chem., 21 (3) pp. 479–496, (1991).
T. P. Ahern et al., Can. J. Chem. 55, 1701 (1977).
M. A. Kelly et al., J. Chem. Soc., Perkin Trans. II, 1649 (1982).
Derwent Abstract AN 72-63513T 1973.
Derwent Abstract AN 89-035266 Dec. 1988.
Derwent Abstract AN 90-005254 Nov. 21, 1989.

*Primary Examiner*—Paul F. Shaver
*Attorney, Agent, or Firm*—Martin Connaughton

[57] ABSTRACT

Organosiloxanes comprising at least one chemically bonded transition metal complex of Pt, Pd, Rh, Ru, Os or Ir, having a triazene, tetrazene, tetrazdiene, pentazdiene or triazene oxide ligand and are used as hydrosilylation catalysts that can be activated by light and/or heat.

6 Claims, No Drawings

ORGANOSILOXANE-BONDED TRANSITION METAL COMPLEXES

FIELD OF INVENTION

The present invention relates to organosiloxane-bonded transition metal complexes, processes for the preparation thereof and cross-linkable compositions which comprise the organosiloxane-bonded transition metal complexes as homogeneous hydrosilylation catalysts.

BACKGROUND OF INVENTION

It is known that the addition of Si-bonded hydrogen to an aliphatic multiple bond, which is described as hydrosilylation, can be promoted by transition metal catalysts, in particular platinum compounds. Reference is made to U.S. Pat No. 5,187,134 in which polymeric complexes of metals of subgroup VIII of the Periodic Table having organosiloxane-phenylphosphine ligands are used as heterogeneous hydrosilylation catalysts.

U.S. Pat. No. 5,175,325 describes platinum organosiloxane complexes which dissolve in addition-cross-linking organosiloxane compositions. The organosiloxane compositions cross-link at room temperature or can be stabilized by an inhibitor in such a way that they only cross-link on heating.

Triazenido, tetrazenido, tetrazdienido and pentazdienido transition metal complexes are known from D. S. Moore et al., Advances in Inorganic Chemistry and Radiochemistry, Vol. 30, pages 1-68, 1986.

Triazene-1-oxide transition metal complexes are known from Tandon et al., Synth. React. Inorg. Met.-Org. Chem., 21 (3), pages 479-496, (1991).

SUMMARY OF INVENTION

It is an object of the present invention to provide catalysts which readily dissolve in addition-cross-linking organosiloxane compositions, are stable in such compositions without inhibitor at room temperature in the absence of light, but after activation by heat and/or light promote the molecular addition of Si-bonded hydrogen to an aliphatic multiple bond.

The present invention provides organosiloxanes which comprise at least one chemically bonded transition metal complex of Pt, Pd, Rh, Ru, Os or Ir which has a triazene, tetrazene, tetrazdiene, pentazdiene or triazene oxide ligand.

Preferred organosiloxanes of the invention are organosiloxanes which are built up of at least two units of the formula $$B_m R_n SiO_{\frac{4-n-m}{2}}, \quad (1)$$

in which
B is a radical of the formula $$MX_a Y_b Z_c \quad (2),$$

where
M is Pt, Pd, Rh, Ru, Os or Ir,
X is a triazene, tetrazene, tetrazdiene, pentazdiene or triazene oxide ligand selected from the group consisting of ANNNR$^1$, ANNNR$_1$R$^2$, ANNNA$^1$, ANR$^2$NNNR$^3$A$^1$, ANNNNA$^1$, ANNNR$^4$NNA$^1$, ANNNNNA$^1$ and ANNNOR$^1$, where
R is a monovalent, substituted or unsubstituted hydrocarbon radical having from 1 to 18 carbon atoms per radical,
R$^1$ is a monovalent, substituted or unsubstituted hydrocarbon radical having from 1 to 18 carbon atoms per radical or a radical of the formula —SiR$^5_d$(OR$^5$)$_{3-d}$,
R$^2$, R$^3$ and R$^4$ are identical or different and are a hydrogen atom or a monovalent, substituted or unsubstituted hydrocarbon radical having from 1 to 18 carbon atoms per radical, and
A and A$^1$ are identical or different and are a radical of the formula

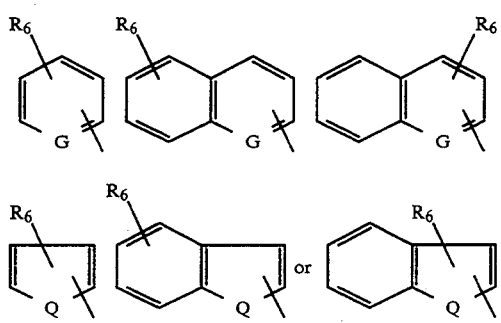

where
G is CH or N and
Q is S, O or NH,
R$^6$ is a monovalent, substituted or unsubstituted hydrocarbon radical having from 1 to 12 carbon atoms per radical, or a radical of the formula —F, —Cl, —Br, —I, —H, —NH$_2$, —NR$^6_2$, —NO$_2$, —OH, —OR$^5$, —SH, —CN, —COOH, —COCl, —CONH$_2$, —COR$^5$, —CHO, —SO$_2$NHR$^5$, —SO$_3$H, —SO$_2$Cl or —R$^7$—SiR$^5_d$(OR$^5$)$_{3-d}$,
R$^5$ is identical or different and is an alkyl radical having from 1 to 8 carbon atoms per radical and
R$^7$ is a divalent hydrocarbon radical having from 1 to 8 carbon atoms per radical,
d is 0, 1, 2 or 3,
Y is identical or different and is a ligand selected from the group consisting of Cl, Br, I, NH$_3$, PR$_3$, H, CO, 1,5-cyclooctadiene, pyridine, bipyridine, acetate, acetylacetonate, phenyl cyanide, ethylenediamine, acetonitrile, 2,5-norbornadiene, nitrate, nitrite, H$_2$O, benzene, diphenylphosphinoethane and 1,3-divinyl-1,1,3,3-tetramethyldisiloxane, is identical or different and is a ligand radical selected from the group consisting of Sp—NH$_2$, Sp—NR$^{10}_2$, Sp—NR$^{10}$(R$^7$)NR$^{10}_2$, Sp-4-pyridine, Sp-2-bipyridine,
Sp-4-bipyridine, Sp—PR$^{10}$(R$^7$)PR$^{10}_2$, Sp—PR$^{10}_2$, Sp-POR$^{10}_2$, Sp—P(OR$^{10}$)$_2$, Sp—SH and Sp—SR$^{10}$,
R$^{10}$ is a hydrogen atom or an alkyl radical having from 1 to 6 carbon atoms,
Sp is a divalent, SiC-bonded, substituted or unsubstituted hydrocarbon radical having from 1 to 18 carbon atoms per radical,
a is 1, 2, 3 or 4,
b is 0 or an integer from 1 to 4,
c is 1, 2, 3 or 4 and
m and n are idential or different and are 0 or an integer from 1 to 3.

Preferred organosiloxanes of the invention are also organosiloxanes which are built up of at least two units of the formula $$B'_m R_n SiO_{\frac{4-n-m}{2}}, \quad (3)$$

in which
B' is a radical of the formula $$MX'_e Y_f \quad (4),$$

where
X' is a triazene, tetrazene, pentazdiene or triazene oxide ligand radical selected from the group consisting of ANNNSp, ANNNSpR$^2$, ANNSpNA$^1$, ANSpNNNR$^3$A$^1$, ANNNSpNNA$^1$, and ANNNOSp,
e is 1, 2, 3 or 4,
f is 0 or an integer from 1 to 6 and
R, M, Y, Sp, R$^1$, R$^2$, R$^3$, R$^4$, R$^5$, R$^6$, R$^7$, A, A$^1$, d, m and n are as defined above.

Examples of hydrocarbon radicals R, R$^1$, R$^2$, R$^3$, R$^4$ and R$^6$ are alkyl radicals such as the methyl, ethyl, n-propyl, iso-propyl, n-butyl, iso-butyl, tert-butyl, n-pentyl, iso-pentyl, neo-pentyl, tert-pentyl radical; hexyl radicals such as the n-hexyl radical; heptyl radicals such as the n-heptyl radical; octyl radicals such as the n-octyl radical and iso-octyl radicals, such as the 2,2,4-trimethylpentyl radical; nonyl radicals such as the n-nonyl radical; decyl radicals such as the n-decyl radical; dodecyl radicals such as the n-dodecyl radical; and octadecyl radicals such as the n-octadecyl radical; cycloalkyl radicals such as the cyclohexyl radical; alkenyl radicals such as the vinyl, 1-propenyl, 1-butenyl, 2-butenyl, allyl, iso-butenyl, 1-pentenyl and 2-methyl-1-butenyl radical; alkynyl radicals such as the ethynyl, propargyl, 1-propynyl and 1-butynyl radical, and aralkyl radicals such as the benzyl radical and the α- and β-phenylethyl radical; with alkyl radicals being preferred.

Examples of substituted hydrocarbon radicals are haloalkyl radicals such as the 3,3,3-trifluoro-n-propyl radical, the 2,2,2,2',2',2'-hexafluoroisopropyl radical, the heptafluoroisopropyl radical, the 3-chloro-n-propyl radical, 2-ethyl bromide and 3-propyl bromide; haloaryl radicals such as the o-, m- and p-chlorophenyl radical, o-, m- and p-bromophenyl radical; substituted aryl radicals such as the 4-cyanophenyl, 4-nitrophenyl and 4-methoxyphenyl radical; hydroxyalkyl radicals such as the radicals of the formulae HOCH$_2$CH$_2$OCH$_2$CH$_2$—, HOCH$_2$CH$_2$— and CH$_3$CH$_2$CH(OH)CH$_2$—; aminoalkyl radicals such as the aminomethyl and aminoethyl radical; carboxyalkyl radicals such as the radicals of the formulae —(CH$_2$)$_7$COOH, —(CH$_2$)$_8$COOH and —CH$_2$COCH$_2$CH$_2$COOH and also their esters and amides —(CH$_2$)$_7$COOCH$_3$, —(CH$_2$)$_7$COOC$_2$H$_5$, —(CH$_2$)$_7$CONH$_2$, —(CH$_2$)$_8$COOCH$_3$, —(CH$_2$)$_8$COOC$_2$H$_5$, —(CH$_2$)$_8$CONH$_2$ and a radical of the formula —CH(COOC$_2$H$_5$)$_2$; carboxyaryl radicals such as the 4-carboxyphenyl, 3-carboxyphenyl radical and radicals of the formulae 4-CH$_3$OCOC$_6$H$_4$—, 4-C$_2$H$_5$OCOC$_6$H$_4$— and 4-H$_2$NCOC$_6$H$_4$—; and substituted aralkyl radicals such as the substituted benzyl radical and the substituted α- and β-phenylethyl radical.

The above examples of alkyl radicals also apply to R$^5$.

The above examples of alkyl radicals having from 1 to 6 carbon atoms also apply to R$^{10}$.

The radicals R$^6$ are substituents of the aromatic and heteroaromatic radical A or A$^1$ and can be in the ortho, meta or para position if A or A$^1$ is an aromatic 6-membered ring, such as a phenyl radical.

Examples of divalent hydrocarbon radicals R$^7$ and Sp are saturated alkylene radicals such as the methylene and ethylene radical and also propylene, butylene, pentylene, hexylene, cyclohexylene and octadecylene radicals or unsaturated alkylene or arylene radicals such as the hexenylene radical and phenylene radicals.

Particularly preferred organosiloxanes units of formula 1 possess, as ligand X in formula 2, a triazene, pentazdiene or triazene oxide ligand ANNNR$^1$, ANNNNNA$^1$ and ANNNOR$^1$, in which A and A$^1$ are phenyl, naphthyl and furanyl radicals and R$^1$ are methyl, hexyl, octyl and dodecyl radicals.

Preferred ligand radicals Z are Sp—NR$^{10}_2$ and Sp—NR$^{10}$(R$^7$)—NR$^{10}_2$, where R$^{10}$ is a hydrogen atom or an alkyl radical having from 1 to 6 carbon atoms and R$^7$ is an alkylene radical.

a is preferably 1, 2, 3 or 4, c is preferably 1 or 2 and b is preferably 0.

Particularly preferred organosiloxanes units of formula 3 possess, as ligand radical X' in formula 4, a triazene ligand radical ANNN-Sp, in which A is a p-nitrophenyl or p-cyanophenyl radical.

e is preferably 1 or 2 and f is preferably 0 or 3.

In the organosiloxanes of formulas 1 or 3, preferred radicals Sp are a divalent alkylene radical having from 2 to 8 carbon atoms, with the n-propylene radical being more preferred.

The preferred transition metals M are Pt, Pd and Rh.

In the organosiloxanes of units of formula 1 or 3, preferably at least 50 mol %, in particular at least 90 mol % of the units have m equal to 0 and n equal to 2. In particular, the organosiloxanes of the invention are preferably linear.

Preferred examples of the triazene ligand X, in particular ANNNR, are those of the formulae C$_6$H$_5$NNN(CH$_2$)$_x$CH$_3$, p-NO$_2$—C$_6$H$_4$NNN(CH$_2$)$_x$CH$_3$, p-CN—C$_6$H$_4$NNN(CH$_2$)$_x$CH$_3$ and p-CH$_3$(CH$_2$)$_x$—C$_6$H$_4$NNN(CH$_2$)$_x$CH$_3$, where x is 1, 3, 5, 7, 11 and 17, more preferably 1, 5, 7 and 11.

Preferred examples of the ligands ANNNNNA$^1$ are those of the formulae p-Br—C$_6$H$_4$NNNNNC$_6$H$_4$—Br-p and p-CH$_3$O—C$_6$H$_4$NNNNNC$_6$H$_4$—OCH$_3$-p.

Preferred examples of the triazene oxide ligand X, in particular ANNN(O)R$^1$ are those of the formulae C$_6$H$_5$NNN(O)CH$_3$ and p-CH$_3$(CH$_2$)$_x$—C$_6$H$_4$NNN (O) CH$_3$.

Preferred examples of catalysts are those of the formulae

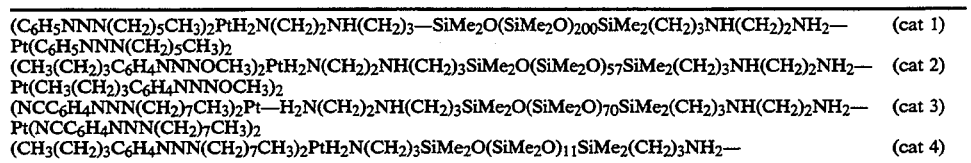

| | |
|---|---|
| (C$_6$H$_5$NNN(CH$_2$)$_5$CH$_3$)$_2$PtH$_2$N(CH$_2$)$_2$NH(CH$_2$)$_3$—SiMe$_2$O(SiMe$_2$O)$_{200}$SiMe$_2$(CH$_2$)$_3$NH(CH$_2$)$_2$NH$_2$—Pt(C$_6$H$_5$NNN(CH$_2$)$_5$CH$_3$)$_2$ | (cat 1) |
| (CH$_3$(CH$_2$)$_3$C$_6$H$_4$NNNOCH$_3$)$_2$PtH$_2$N(CH$_2$)$_2$NH(CH$_2$)$_3$SiMe$_2$O(SiMe$_2$O)$_{57}$SiMe$_2$(CH$_2$)$_3$NH(CH$_2$)$_2$NH$_2$—Pt(CH$_3$(CH$_2$)$_3$C$_6$H$_4$NNNOCH$_3$)$_2$ | (cat 2) |
| (NCC$_6$H$_4$NNN(CH$_2$)$_7$CH$_3$)$_2$Pt—H$_2$N(CH$_2$)$_2$NH(CH$_2$)$_3$SiMe$_2$O(SiMe$_2$O)$_{70}$SiMe$_2$(CH$_2$)$_3$NH(CH$_2$)$_2$NH$_2$—Pt(NCC$_6$H$_4$NNN(CH$_2$)$_7$CH$_3$)$_2$ | (cat 3) |
| (CH$_3$(CH$_2$)$_3$C$_6$H$_4$NNN(CH$_2$)$_7$CH$_3$)$_2$PtH$_2$N(CH$_2$)$_3$SiMe$_2$O(SiMe$_2$O)$_{11}$SiMe$_2$(CH$_2$)$_3$NH$_2$— | (cat 4) |

-continued

| | |
|---|---|
| Pt(CH₃(CH₂)₃C₆H₄NNN(CH₂)₇CH₃)₂ | |
| (C₆H₅NNN(CH₂)₅CH₃)₂PdH₂N(CH₂)₂NH(CH₂)₃SiMe₂O(SiMe₂O)₂₀₀SiMe₂(CH₂)₃NH(CH₂)₂NH₂—Pd(C₆H₅NNN(CH₂)₅CH₃)₂ | (cat 5) |
| (BrC₆H₄NNNNNC₆H₄Br)₂PtH₂N(CH₂)₂NH(CH₂)₃SiMe₂O(SiMe₂O)₂₀₀SiMe₂(CH₂)₃NH(CH₂)₂NH₂—Pt(BrC₆H₄NNNNNC₆H₄Br)₂ | (cat 6) |
| ⁻(Pt—NNNC₆H₄CN—(CH₂)₃—SiMe₂O(SiMe₂O)₁₁—SiMe₂(CH₂)₃—NCC₆H₄NNN)ᵧ  y = 7 to 8 | (cat 7) |
| (PPh₃)₃Rh—NNNC₆H₄NO₂—(CH₂)₃—SiMe₂O(SiMe₂O)₁₁SiMe₂(CH₂)₃—O₂NC₆H₄NNN—Rh(PPh₃)₃ | (cat 8) |

The invention further provides a process for preparing the organosiloxanes of formula 1, in which organosiloxanes which comprise at least one bonded transition metal complex of Pt, Pd, Rh, Ru, Os or Ir and which are built up of at least two units of the formula $$G_m R_n SiO_{\frac{4-n-m}{2}}, \quad (5)$$

in which
G is a radical of the formula $$MY_g Z_c \quad (6),$$

where n, m, R, M, Y, Z and c are as defined above and
g is an integer from 1 to 8, are reacted in the presence of a base with triazene, tetrazene, pentazdiene or triazene oxide compounds selected from the group consisting of ANNNHR¹, ANNNHR², ANNNHA¹, ANHNNNHA¹, ANNNHNNA¹ and ANNNOHR¹, or in the absence of base with triazene, tetrazene, tetrazdiene, pentazdiene or triazene oxide compounds selected from the group consisting of ANNNR¹R², ANNNR¹A¹, ANR²NNNR³A¹, ANNNR⁴NNA¹ and ANNNNA¹, where R¹, R², R³, R⁴, A and A¹ are as defined above.

The invention further provides a process for preparing the organosiloxanes of formula 3, wherein organosiloxanes which comprise at least one triazene, tetrazene, pentazdiene or triazene oxide radical and which are built up of at least two units of the formula $$X''_m R_n SiO_{\frac{4-n-m}{2}}, \quad (7)$$

in which
X" is a triazene, tetrazene or triazene oxide radical selected from the group consisting of ANNNHSp, ANHNNNSpA¹ and ANNNOHSp, are reacted in the presence of a base with a transition metal halide complex of the formula $$MY_h Hal_i \quad (8),$$

or
X" is a triazene, tetrazene, pentazdiene or triazene oxide radical selected from the group consisting of ANNNRSp, ANNNSpNa, ANSpNNNR³A¹, and ANNNSpNNA¹, in the absence of a base with a transition metal complex of the formula $$MY_j \quad (9),$$

where
A, A¹, Sp, R, M, Y, m and n are as defined above,
Hal is a chlorine, bromine or iodine atom,
h is 1, 2, 3 or 4,
i is 0 or an integer from 1 to 6 and
j is an integer from 1 to 8.

Examples of bases which are used in the preparation of the organosiloxanes of formulae 1 and 3 are n-butyllithium, triethylamine, piperidine, pyridine, NaOCH₃ and NaNH₂, with n-butyllithium and triethylamine being preferred.

The process for preparing the organosiloxanes of formulae 1 and 3 is preferably carried out in the presence of organic solvents such as n-hexane, toluene, methylene chloride, chloroform, acetone or tetrahydrofuran, but can also be carried out in the presence of a mixture of water and organic solvent such as methanol, ethanol, isopropanol or preferably tetrahydrofuran (THF).

The process for preparing the organosiloxanes of formulae 1 and 3 is preferably carried out at temperatures of from −20° C. to 30° C., at the pressure of the surrounding atmosphere and with exclusion of light. The organic solvent or the mixture of organic solvent and water is preferably removed after the reaction.

The preparation of the triazenido complexes of transition metals, with the exception of the arylalkyltriazenido complexes of transition metals, the tetrazenido complexes of transition metals, the tetrazdienido complexes of transition metals and the pentazdienido complexes of transition metals is known and described in D. S. Moore et al., Advances in Inorganic Chemistry and Radiochemistry, Vol 30, pages 1–68, 1986.

The preparation of the triazenes, tetrazenes, tetrazdienes and pentazdienes is known and described in T. P. Ahern et al., Can. J. Chem. 55, 1701 (1977) and M. A. Kelly et al., J. Chem. Soc., Perkin Trans. II, 1649 (1982).

Examples of triazenes of the formula ANNNHR¹ which are used in the preparation of the arylalkyltriazenido complexes of formula 6 are C₆H₅NNNH(CH₂)ₓCH₃, p-NO₂—C₆H₄NNNH(CH₂)ₓCH₃, p-CN—C₆H₄NNNH(CH₂)ₓCH₃, p-CH₃—C₆H₄NNNH(CH₂)ₓCH₃, p-CH₃(CH₂)ₓC₆H₄NNNH(CH₂)ₓCH₃, p-H₃COCO—C₆H₄NNNH(CH₂)ₓCH₃, p-CH₃NHCO—C₆H₄NNNH(CH₂)ₓCH₃, p-CH₃O—C₆H₄NNNH(CH₂)ₓCH₃, p-(CH₃)₂N—C₆H₄NNN(CH₂)ₓCH₃, where C₆H₅NNNH(CH₂)ₓCH₃, p-NO₂—C₆H₄NNNH(CH₂)ₓCH₃, p-CN—C₆H₄NNNH(CH₂)ₓCH₃ and p-CH₃(CH₂)ₓ—C₆H₄NNNH(CH₂)ₓCH₃ are preferred.

Preferably, x is 1, 3, 5, 7, 11 and 17, more preferably 1, 5, 7 and 11.

The organosiloxanes units of formula 5 above can be prepared from organosiloxanes of at least two units of the formula $$Z_m R_n SiO_{\frac{4-n-m}{2}}, \quad (10)$$

in which

Z, R, m and n are as defined above, by reaction with transition metal complexes of formula 9.

Examples of transition metal compounds of formula 8 are $PtCl_2$, $PtI_2$, $[(C_6H_5)_3P]_2PtCl_2$, $[(C_2H_5)_3P]_2PtCl_2$, $PtCl_4$, $Pt(H_2NCH_2CH_2NH_2)Cl_2$, $Pt(NH_3)_2Cl_2$, $PtBr_2$, $PtI_2$, $Na_2PtCl_4$, $Na_4PtCl_6$, 1,5-cyclooctadiene. $PtCl_2$, $Pd(CH_3CN)_2Cl_2$, $PdBr_2$, 1,5-cyclooctadiene. $PdCl_2$, $[(C_6H_5)_3P]_2PdCl_2$, $PdCl_2$, $RuCl_3$, $Ru(NH_3)_6Cl_2$, $[(C_6H_5)_3P]_3RuCl_2$, $RhCl_3$, $RhBr_3$, $[(C_6H_5)_3P]_3RhCl$, (1,5-cyclooctadiene)$_2$Pt, products of subgroup metal halides with olefins, 1,3-divinyl-1,1,3,3-tetramethyldisiloxane platinum complex (e.g. $Pt_2$[1,3-divinyl-1,1,3,3-tetramethyldisiloxane]$_3$), Pd[bis-(1,2-diphenylphosphinoethane)], hexarhodium hexadecacarbonyl and triruthenium dodecacarbonyl, with $PtCl_4$, 1,5-cyclooctadiene.$PtCl_2$, $PtI_2$, 1,3-divinyl-1,1,3,3-tetramethyldisiloxane platinum complex, $PdCl_2$, $[(C_6H_5)_3P]_3RuCl_2$ and $[(C_6H_5)_3P]_3RhCl$ being preferred.

The organosiloxanes units of formula 7 can be prepared from organosiloxanes of at least two units of the formula

$(H_2NSp)_m R_n SiO_{\frac{4-n-m}{2}}$,  (11)

where

Sp, R, n and m are as defined above, by reaction with the corresponding diazonium salts. For the preparation of the triazenidosiloxanes of formula 11, diazonium salt of the formula $AN_2^+BF_4^\ominus$ is used, with A being as defined above.

The organosiloxanes of the invention can be used as catalysts in all cross-linkable organopolysiloxane compositions where catalysts which promote the molecular addition of Si-bonded hydrogen to aliphatic multiple bonds could be used. The organosiloxanes of the invention can be activated by heating at temperatures of from 50° C. to 250° C. and/or by irradiation with light.

The invention provides cross-linkable organopolysiloxane compositions comprising (A) organopolysiloxanes which comprise radicals having aliphatic carbon-carbon multiple bonds, (B) organopolysiloxanes having Si-bonded hydrogen atoms or, instead of (A) and (B)

(C) organopolysiloxanes which comprise radicals having aliphatic carbon-carbon multiple bonds and Si-bonded hydrogen atoms, and (D) as catalysts, organosiloxanes of the invention.

For the purpose of the present invention, radicals having aliphatic carbon-carbon multiple bonds also include radicals having cycloaliphatic carbon-carbon multiple bonds.

The organopolysiloxanes (A), which comprise radicals having aliphatic carbon-carbon multiple bonds, used are preferably linear or branched organopolysiloxanes of units of the formula

$R_k^8 R_l^9 SiO_{\frac{4-k-l}{2}}$,  (11)

where $R^8$ is a monovalent hydrocarbon radical free of aliphatic carbon multiple bonds and having from 1 to 18 carbon atoms per radical and $R^9$ is a monovalent hydrocarbon radical having an aliphatic carbon-carbon multiple bond and having from 2 to 8 carbon atoms per radical, k is 0, 1, 2 or 3, l is 0, 1 or 2 and the sum k+l is 0, 1, 2 or 3, with the proviso that on average there are at least 2 radicals $R^9$ present per molecule. The organopolysiloxanes (A) preferably possess an average viscosity of from 100 to 10,000 mPa.s at 25° C.

Examples of hydrocarbon radicals $R^8$ are alkyl radicals such as the methyl, ethyl, n-propyl, iso-propyl, n-butyl, iso-butyl, tert-butyl, n-pentyl, iso-pentyl, neopentyl, tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such a the n-dodecyl radical; octadecyl radicals such as the n-octadecyl radical; cycloalkyl radicals such as cyclopentyl, cyclohexyl, cycloheptyl radicals and methylcyclohexyl radicals; aryl radicals such as the phenyl, napthyl, anthryl and phenanthryl radical; alkaryl radicals such as o-, m-, and p-tolyl radicals, xylyl radicals and ethylphenyl radicals; and aralkyl radicals such as the benzyl radical, the α- and the β-phenylethyl radical.

Examples of radicals $R^9$ are alkenyl radicals such as the vinyl, 5-hexenyl, 1-propenyl, allyl, 1-butenyl and 1-pentenyl radical and alkynyl radicals such as the ethynyl, propargyl and 1-propynyl radical.

The organopolysiloxanes (B), which have Si-bonded hydrogen atoms, are preferably linear, cyclic or branched organopolysiloxanes of units of the formula

$R_o^8 H_p SiO_{\frac{4-o-p}{2}}$,  (12)

where $R^8$ is as defined above, o is 0, 1, 2 or 3, p is 0, 1 or 2 and the sum of o+p is 0, 1, 2 or 3, with the proviso that on average at least 2 Si-bonded hydrogen atoms are present per molecule. The organopolysiloxanes (B) preferably possess an average viscosity of from 10 to 1,000 mPa.s at 25° C.

The organopolysiloxanes (C), which have aliphatic carbon-carbon multiple bonds and Si-bonded hydrogen atoms and can be used instead of organopolysiloxanes (A) and (B), are preferably those of units of the formulae

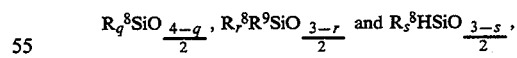
$R_q^8 SiO_{\frac{4-q}{2}}$, $R_r^8 R^9 SiO_{\frac{3-r}{2}}$ and $R_s^8 HSiO_{\frac{3-s}{2}}$, where $R^8$ and $R^9$ are as defined above, q is 0, 1, 2 or 3, r is 0, 1 or 2, s is 0, 1 or 2, with the proviso that per molecule there are present on average at least 2 radicals $R^8$ and on average at least 2 Si-bonded hydrogen atoms.

Examples of organopolysiloxanes (C) are those of $SiO_{4/2}$, $R^8_3SiO_{\frac{1}{2}}$, $R^8_2R^9SiO_{\frac{1}{2}}$ and $R^8_2HSiO_{\frac{1}{2}}$ units, so-called MQ resins, with these resins being able to comprise T units ($R^8SiO_{3/2}$) and D units ($R^8_2SiO$).

The organopolysiloxanes (C) preferably possess an average viscosity of from 100 to 100,000 mPa.s at 25° C. or are solids having molecular weights of from 5,000 to 50,000 g/mol.

Above a molecular mass of 1,000 g/mol, the volatility and migration ability of the organosiloxanes D of the invention used as catalysts are small.

The organosiloxanes (D) of the invention are preferably used in amounts of from 1 to 1,000 ppm by weight (parts by weight per one million parts by weight), preferably from 10 to 100 ppm by weight, in each case calculated as elemental transition metal Pt, Pd, Ru, Rh, Os or Ir and based on the total weight of the organopolysiloxanes (A) and (B) or on the total weight of the organopolysiloxanes (C).

Although not preferred, inhibitors can also be used in the cross-linkable organopolysiloxane compositions. Examples of inhibitors are 1,3-divinyl-1,1,3,3-tetramethyldisiloxane, benzotriazole, dialkylformamides, alkylthioureas, methyl ethyl ketoxime, organic or organosilicon compounds having a boiling point of at least 25° C. at 1012 mbar (abs.) and at least one aliphatic triple bond in accordance with U.S. Pat. No. 3,445,420, such as 1-ethynylcyclohexan-1-ol, 2-methyl-3-butyn-2-ol, 3-methyl-1-pentyn-3-ol, 2,5-dimethyl-3-hexyn-2,5-diol and 3,5-dimethyl-1-hexyn-3-ol, inhibitors in accordance with U.S. Pat. No. 2,476,166, such as a mixture of diallyl maleate and vinyl acetate, and inhibitors in accordance with U.S. Pat. No. 4,504,645, such as maleic monoesters.

The organosiloxanes of the invention can be used in all processes for reacting organosilicon compounds having Si-bonded hydrogen atoms with organic compounds having aliphatic multiple bonds, in which it has also been possible to use catalysts promoting the molecular addition of Si-bonded hydrogen to aliphatic multiple bonds. For the purpose of the present invention, organic compounds having aliphatic multiple bonds include organic compounds having cycloaliphatic multiple bonds.

Examples of organosilicon compounds having one Si-bonded hydrogen atom per molecule such as trichlorosilane, dimethylchlorosilane, dimethylethoxysilane, methyldiethoxysilane, methyldichlorosilane and triethoxysilane, and organopolysiloxanes having at least one Si-bonded hydrogen atom per molecule such as α,w-dihydrogen[dimethylpolysiloxane], tetramethyldisiloxane, tetramethylcyclotetrasiloxane, mixed polymers of trimethylsiloxane units and methylhydrogensiloxane units, mixed polymers of trimethylsiloxane units, dimethylsiloxane units and methylhydrogensiloxane units and trimethylsiloxyhydrogensilane. Examples of organic compounds having aliphatic multiple bonds are compounds having an aliphatic carbon-carbon double bond such as styrene, allyl glycidyl ether, allyl cyanide, allyl acetate, allylsuccinic anhydride, glycol monoallyl ether, allyl methacrylate, allylamine and cyclohexene and compounds having an aliphatic carbon-carbon triple bond such as acetylene and butynol.

In the following examples, unless otherwise indicated,
(a) all amounts are by weight;
(b) all pressures are 0.10 mPa (abs.);
(c) all temperatures are 20° C.

EXAMPLES

Preparation of the triazene (in an aqueous system): 0.25 mol of the aniline derivative specified in each case in Table 1 below was dissolved in 200 ml of 10% strength aqueous hydrochloric acid, then stirred with 1 g of activated carbon for 5 minutes, and filtered. The filtrate was, at 0° C. with exclusion of light, mixed with a solution of 17.25 g (0.25 mol) of sodium nitrite in 30 g of water. After 15 minutes, 1 mol of the alkylamine specified in each case in Table 1 was added dropwise at 0° C. and the mixture was stirred at room temperature for 2 hours. After addition of organic solvent, the mixture was shaken with 3×50 ml of water (or, if necessary, with dilute acetic acid) and the organic phase was dried over sodium sulfate. After filtration, the solution was evaporated in a rotary evaporator at room temperature under reduced pressure. Possible amounts of pentazdiene by-products can be separated off in methanolic solution at −65° C. as a solid. The products specified in Table 1 were obtained at yields of between 60% and 80%.

Preparation of the triazenes (in an organic system): 0.2 mol of the aniline derivative in each case specified in Table 1 was dissolved in 100 ml of acetone, then stirred with 1 g of activated carbon for 5 minutes and filtered. The filtrate was, at −5° C. with exclusion of light and moisture, mixed with 24.59 g (0.25 mol) of anhydrous sulfuric acid and the mixture was stirred for 20 minutes. 20.62 g (0.2 mol) of n-butyl nitrite were then added dropwise and the mixture was stirred for an additional 2 hours at 0° C. Finally, 0.5 mol of the alkylamine in each case specified in Table 1 was added dropwise and the mixture was stirred for an additional 2 hours. The organic phase was shaken 3 times with 50 ml of aqueous hydrochloric acid, dried over sodium sulfate and evaporated to constant weight in a rotary evaporator under reduced pressure. The products specified in Table 1 were obtained in yields of between 70% and 80%.

TABLE 1

| Aniline Derivative | Alkylamine | Triazene |
|---|---|---|
| Aniline | n-hexylamine | 1-phenyl-3-n-hexyl-1-triazene |
| p-nitroaniline | n-octylamine | 1-[4-nitrophenyl]-3-n-octyl-1-triazene |
| p-cyanoaniline | n-octylamine | 1-[4-cyanophenyl]-3-n-octyl-1-triazene |
| p-butylaniline | n-octylamine | 1-[4-butylphenyl]-3-n-octyl-1-triazene |
| p-butylaniline | methyl-hydroxyl-amine | 1-[4-butylphenyl]-3-methyl-1-triazene-3-oxide |

Preparation of the Pentazdienes:

20 mmol of the aniline derivative in each case specified in Table 2 were dissolved in 40 ml of 10% strength aqueous hydrochloric acid (109 mmol), stirred with 0.5 g of activated carbon for 5 minutes and filtered. The filtrate was, at −5° C. with exclusion of light, mixed with a solution of 1.38 g (20 mmol) of sodium nitrite in 10 ml of water, and after 15 minutes 10 ml of a 25% strength ammonia solution (147 mmol) were metered in at 0° C. The mixture was stirred at room temperature for 1 hour. After addition of 100 ml of organic solvent, the mixture was shaken three times with 50 ml of water (or, if necessary, with dilute acetic acid) and the organic phase was dried over sodium sulfate. The pentazdienes were reacted without purification (danger of explosion) with the transition metals.

TABLE 2

| Aniline Derivative | Product |
|---|---|
| Aniline | 1,5-diphenyl-1,4-pentazdiene |

TABLE 2-continued

| Aniline Derivative | Product |
|---|---|
| p-bromoaniline | 1,5-di[4-bromophenyl]-1,4-pentazdiene |
| p-methoxyaniline | 1,5-di[4-methoxyphenyl]-1,4-pentazdiene |

Preparation of the catalyst precursors P1:

1 mmol of the α,w-aminoethylaminopropyldimethylpolysiloxanes (chain length 57, 70, 200) was dissolved in 100–500 ml of THF (tetrahydrofuran), then mixed with 2 mmol (0.75 g) of cyclooctadienedichloroplatinum (II) or 2 mmol (0.355 g) of palladium dichloride and the mixture was heated for 4–8 hours under reflux and subsequently filtered. The filtrate was evaporated to constant weight in a high vacuum at 100° C. The yellow, oily to elastically solid products were obtained in yields of between 90% and 99%.

Preparation of the catalyst precursors P2:

1 mmol of the α,w-aminopropyldimethylpolysiloxanes (chain length 11, 70) was dissolved in 100–300 ml of THF, then mixed with 2 mmol (0.75 g) of cyclooctadienedichloroplatinum(II), the mixture was heated for 4–8 hours under reflux and subsequently filtered. The filtrate was evaporated to constant weight in a high vacuum at 100° C. The elastically solid products were obtained in yields of between 90% and 95%.

Preparation of the catalyst precursors P3:

66.3 mmol of the aniline derivative in each case specified in Table 1 were dissolved in 250 ml of 10% strength hydrochloric acid, then stirred with 1 g of activated carbon for 5 minutes and filtered. The filtrate was, at 0° C. with exclusion of light, mixed with a solution of 4.58 g (66.3 mmol) of sodium nitrite in 10 ml of water. After 15 minutes, 7.5 g (66.3 mmol) of sodium tetrafluoroborate dissolved in 20 ml of water were added at 0° C. and the mixture was stirred for 30 minutes at −5° C. The precipitate was filtered off with suction and added to a solution of 22.1 mmol of α,w-aminopropyldimethylsiloxane (chain length 11, 70) and 6.7 g (66.3 mmol) of triethylamine in 50 g of THF at −5° C. Over a period of 3 hours, the solution became deep red in color. After filtration, the mixture was evaporated in a rotary evaporator at room temperature under reduced pressure, mixed with diethyl ether and the product was kept at 4° C. for 24 hours. After pressure filtration and evaporation of the solvent, yellow to red colored oils were obtained in yields of 80%–90%.

P1: $Cl_2WH_2NCH_2CH_2NH(CH_2)_3SiMe_2O(SiMe_2O)_xSiMe_2(CH_2)_3NH(CH_2)_2—NH_2PtCl_2$
  x = 57, 70, 200     W = Pd, Pt
P2: $Cl_2PtH_2N(CH_2)_3SiMe_2O(SiMe_2O)_xSiMe_2(CH_2)_3NH_2PtCl_2$
  x = 11, 70
P3: $R^{11}C_6H_4NNNH(CH_2)_3SiMe_2O(SiMe_2O)_xSiMe_2(CH_2)_3NHNNC_6H_4R^{11}$
  x = 11, 70     $R^{11}$ = —CN, —CH$_3$, —NO$_2$, —Cl or —OCH$_3$

Example 1

1.02 g (5 mmol) of 1-phenyl-3-n-hexyl-1-triazene, the preparation of which has been described above, were, with exclusion of light, initially charged with 20 ml of anhydrous THF at −10° C. Under a nitrogen atmosphere, 3.43 ml of a 1.6 molar solution of n-butyllithium (5.5 mmol) in n-hexane were slowly metered in. After 20 minutes, a solution of 15.69 g (1 mmol) of α,w-aminoethylaminopropylpolydimethylsiloxanedichloroplatinum (P1) of chain length 200 in 200 ml of THF were added dropwise and the mixture was stirred for 72 hours at room temperature. The solution was rotary evaporated at room temperature and at reduced pressure, the residue was taken up in 30 ml of toluene, filtered and the filtrate was added to 400 ml of methanol and vigorously stirred. After decanting the supernatant methanol, the procedure was repeated. The highly viscous, yellow to red colored, sedimented product was evaporated to constant weight in a high vacuum at room temperature. 13.1 g (80% yield) of red, highly viscous catalyst (Cat 1) were obtained.

Example 2

The procedure of Example 1 was repeated except that 1.04 g (5 mmol) of 1-p-n-butylphenyl-3-n-methyl-1-triazene 3-hydroxide were used instead of 5 mmol of 1-phenyl-3-methyl-1-triazene and 5.08 g (1 mmol) of α,w-aminoethylaminopropylpolydimethylsiloxanedichloroplatinum of the chain length 57 (P1) were used instead of 1 mmol of P1 of the chain length 200. 5.3 g (92% yield) of the yellow, oily catalyst Cat 2 were obtained.

Example 3

The procedure of Example 1 was repeated except that 1.29 g (5 mmol) of 1-p-cyanophenyl-3-n-octyl-1-triazene were used instead of 5 mmol of 1-phenyl-3-n-hexyl-1-triazene and 6.05 g (1 mmol) of α,w-aminoethylaminopropylpolydimethylsiloxanedichloroplatinum of the chain length 70 (P1) were used instead of 1 mmol of P1 of the chain length 200. 5.90 g (85% yield) of the yellow, oily catalyst Cat 3 were obtained.

Example 4

The procedure of Example 1 was repeated except that 1.44 g (5 mmol) of 1-p-n-butylphenyl-3-n-octyl-1-triazene were used instead of 5 mmol of 1-phenyl-3-n-hexyl-1-triazene and 1.55 g (1 mmol) of α,w-aminopropylpolydimethylsiloxanedichloroplatinum (P2) of the chain length 11 were used instead of 1 mmol of P1 of the chain length 200. 2.1 g (82% yield) of the yellow, solid catalyst Cat 4 were obtained.

Example 5

The procedure of Example 1 was repeated except that instead of 1 mmol of P1 of the chain length 200 having platinum as the central atom, 16.19 g (1 mmol) of α,w-aminoethylaminopropylpolydimethylsiloxanedichloropalladium P1 of the chain length 200 were used. 13.5 g (80% yield) of the yellow, solid catalyst 5 were obtained.

Example 6

The procedure of Example 1 was repeated except that 1.92 g (5 mmol) of 1,5-p-bromophenylpentaz-1,4-diene were used instead of 5 mmol of 1-phenyl-3-n-hexyl-1-triazene. 14.0 g (82% yield) of the yellow, oily catalyst Cat 6 were obtained.

Example 7

1.28 g (1 mmol) of α,w-1-p-cyanophenyl-3-n-propyl-1-triazenepolydimethylsiloxane of the chain length 11

(P3 having $R^{11}$=CN) were, with exclusion of light, initially charged with 30 ml of anhydrous THF at −10° C. Under a nitrogen atmosphere, 1.56 ml (2.5 mmol) of a 1.6 molar solution of n-butyllithium in n-hexane were slowly metered in. After 40 minutes, 0.27 g (1 mmol) of platinum dichloride were added and the mixture was stirred for 72 hours at room temperature. The solution was rotary evaporated at room temperature and at reduced pressure, taken up in 40 ml of diethyl ether, kept for 24 hours at 4° C., filtered and subsequently evaporated to constant weight in a high vacuum at room temperature. 1.25 g (85% yield) of red, highly viscous catalyst Cat 7 were obtained.

Example 8

The procedure of Example 7 was repeated except that 1.33 g (1 mmol) of α,w-1-p-nitrophenyl-3-n-propyl-1-triazenepolydimethylsiloxane of the chain length 11 having $R^{11}$=NO$_2$ (P3) were used instead of 1 mmol of P3 having $R^{11}$ =CN and 1.85 g (2 mmol) of tris[triphenylphosphine]rhodium chloride were used instead of 1 mmol of platinum dichloride. 2.33 g (75% yield) of the red, oily catalyst Cat 8 were obtained.

Example 9

32 mg (1.959×10$^{-6}$ mol) of Cat 1 were dissolved in 0.5 ml of THF and then added to 7.46 g of α,w-divinyldimethylpolysiloxane having a viscosity of 500 mPa.s at 25° C. The solvent was removed at room temperature under reduced pressure. To the remaining reaction mixture was added 0.187 g of a mixed polymer of trimethylsiloxane units and methyl hydrogen siloxane units having a viscosity of 33 mPa.s at 25° C. and containing 1.12% by weight of Si-bonded hydrogen, so that the mixture contained 100 ppm by weight of platinum, calculated as element. The whole mixture was stable for at least 6 weeks at room temperature and with exclusion of light. After irradiation for 15 minutes with ultraviolet light (UVA=56 mW/cm$^2$, UVB=12 mW/cm$^2$), complete cross-linking of the mass (the extractable proportion, i.e., the proportion not crosslinked, is less than 5% by weight) was achieved. A transparent product insoluble in organic solvents was obtained.

Example 10

The procedure of Example 9 was repeated, except that after heating for 73 minutes at 80° C. a complete cross-linking of the mass (the extractable proportion, i.e., the proportion not cross-linked, is less than 5% by weight) was achieved. A transparent product insoluble in organic solvents was obtained.

Example 11

The procedure of Example 9 was repeated, except that after heating for 12.5 minutes at 100° C. a complete cross-linking of the mass (the extractable proportion, i.e., the proportion not cross-linked, is less than 5% by weight) was achieved. A transparent product insoluble in organic solvents was obtained.

Example 12

The procedure of Example 9 was repeated, except that after heating for 4.9 minutes at 120° C. a complete cross-linking of the mass (the extractable proportion, i.e., the proportion not cross-linked, is less than 5% by weight) was achieved. A transparent product insoluble in organic solvents was obtained.

Example 13

The procedure of Example 9 was repeated, except that the α,w-divinyldimethylpolysiloxane used had a viscosity of 1,000 mPa.s at 25° C. instead of 500 mPa.s at 25° C. After irradiation for 15 minutes with ultraviolet light (UVA=56 mW/cm$^2$, UVB=12 mW/cm$^2$), a complete cross-linking of the mass (the extractable proportion, i.e., the proportion not cross-linked, is less than 5% by weight) was achieved. A transparent product insoluble in organic solvents was obtained.

Example 14

The procedure of Example 9 was repeated, except that 11.53 mg (3.7×10$^{-6}$ mol) of Cat 8 were used instead of 32 mg of Cat 1. The mixture contained 100 ppm by weight of rhodium, calculated as element. The total mixture was stable for at least 9 weeks at room temperature and with exclusion of light. After heating for 31 minutes at 180° C., a complete cross-linking of the mass (the extractable proportion, i.e., the proportion not cross-linked, is less than 5% by weight) was achieved. A clear brittle mass was obtained.

Example 15

The procedure of Example 14 was repeated, except that the α,w-divinyldimethylpolysiloxane used had a viscosity of 1,000 mPa.s at 25° C. instead of 500 mPa.s at 25° C. The total mixture was stable for at least 9 weeks at room temperature and with exclusion of light. After heating for 31 minutes at 180° C., a complete cross-linking of the mass (the extractable proportion, i.e., the proportion not cross-linked, is less than 5% by weight) was achieved. A clear brittle mass was obtained.

Example 16

The procedure of Example 9 was repeated, except that 58.17 mg (3,593×10$^{-6}$ mol) of Cat 5 were used instead of 32 mg of Cat 1. The mixture contained 100 ppm by weight of palladium, calculated as element. The total mixture was stable for at least 9 weeks at room temperature and with exclusion of light. After heating for 13 minutes at 170° C., a complete cross-linking of the mass (the extractable proportion, i.e., the proportion not cross-linked, is less than 5% by weight) was achieved. A clear brittle mass was obtained.

Example 17

The procedure of Example 16 was repeated, except that the α,w-divinyldimethylpolysiloxane used had a viscosity of 1,000 mPa.s at 25° C. instead of 500 mPa.s at 25° C. The total mixture was stable for at least 9 weeks at room temperature and with exclusion of light. After heating for 13 minutes at 170° C., a complete cross-linking of the mass (the extractable proportion i.e., the proportion not cross-linked, is less than 5% by weight) was achieved. A clear brittle mass was obtained.

Example 18

In 0.5g of an organopolysiloxane resin of SiO$_2$, trimethylsiloxane, dimethylvinylsiloxane and methylphenylsiloxane units, having a viscosity of 1,600 mPa.s at 25° C. and containing 7.6% by weight of Si-bonded vinyl groups, was dissolved in a solution of 32 mg (1,959×10$^{-6}$ mol) of Cat 1 in 0.5 ml of THF. The solvent was removed at room temperature under reduced pressure, and to the remaining reaction mixture were added 5 g of an organopolysiloxane resin of SiO$_2$, trimethylsiloxane, dimethylhydrogensiloxane and methylphenylsiloxane units, having a viscosity of 2,000 mPa.s at 25° C. and containing 0.2% by weight of Si-bonded hydrogen, so that the mixture contained 100 ppm by weight by platinum, calculated as the element. The total mixture was stable for at least 6 weeks at room temperature and with exclusion of light. With good mixing, complete cross-linking of the mass was achieved after heating for 15 minutes at 170° C. A clear, insoluble substance was obtained.

Example 19

The procedure of Example 9 was repeated, except that 11.30 mg ($1.959 \times 10^{-6}$ mol) of Cat 2 were used instead of 32 mg of Cat 1. The mixture contained 100 ppm by weight of platinum, calculated as element. The total mixture was stable for at least 9 weeks at room temperature and with exclusion of light. With good mixing, complete cross-linking of the mass was achieved after heating for 2.1 minutes at 120° C. A clear insoluble substance was obtained.

Example 20

The procedure of Example 18 was repeated, except that 58.17 mg ($3.593 \times 10^{-6}$ mol) of Cat 5 were used instead of 32 mg of Cat 1. The mixture contained 100 ppm by weight of palladium, calculated as element. The total mixture was stable for at least 9 weeks at room temperature and with exclusion of light. With good mixing, complete cross-linking of the mass was achieved after heating for 30 minutes at 170° C. A clear insoluble substance was obtained.

Example 21

4 g of an organopolysiloxane resin of the formula $(SiO_2)$—$_{610}(Me_3SiO_{\frac{1}{2}})_{232}(EtO_{\frac{1}{2}})_{414}(HMe_2SiO_{\frac{1}{2}})_{156}$-$(ViMe_2SiO_{\frac{1}{2}})_{100}$ were dissolved in 16 g of toluene at room temperature, filtered and while stirring 83.7 mg of Cat 1 were mixed in, so that the mixture contained 100 ppm by weight of platinum, calculated as element. After heating for 10 hours at 60° C., a complete cross-linking of the mass was achieved. A stiff, pale yellow gel was obtained.

Example 22

33.5 mg ($1,959 \times 10^{-6}$ mol) of Cat 6 were dissolved in 0.5 ml of THF and then added to 7.46 g of α,w-divinyldimethylpolysiloxane having a viscosity of 500 mPa.s at 25° C. The solvent was removed at room temperature under reduced pressure. To the remaining reaction mixture was added 0,187 g of a mixed polymer of trimethylsiloxane and methylhydrogensiloxane units, having a viscosity of 33 mPa.s at 25° C. and containing 1.12% by weight of Si-bonded hydrogen, so that the mixture contained 100 ppm by weight of platinum, calculated as element. The total mixture was stable for at least 6 weeks at room temperature and with exclusion of light. After heating for 5 minutes at 100° C., complete cross-linking of the mass (the extractable proportion, i.e., the proportion not cross-linked, is less than 5% by weight) was achieved. A transparent product insoluble in organic solvents was obtained.

Example 23

The procedure of Example 22 was repeated, except that the mixture was cross-linked over a period of 10 minutes by irradiation with ultraviolet light (UVA=56 mW/cm$^2$, UVB=12 mW/cm$^2$) instead of by heating at 100° C.

Example 24

The procedure of Example 9 was repeated, except that 13.60 mg ($1,959 \times 10^{-6}$ mol) of Cat 3 were used instead of 32 mg of Cat 1. The mixture contained 100 ppm by weight of platinum, calculated as element. The total mixture was stable for at least 6 weeks at room temperature and with exclusion of light. After heating for 15 minutes at 100° C., a complete cross-linking of the mass (the extractable proportion, i.e., the proportion not cross-linked, is less than 5% by weight) was achieved. A clear, brittle mass was obtained.

Example 25

The procedure of Example 19 was repeated, except that after irradiation for 4.7 minutes with ultraviolet light (UVA=56 mW/cm$^2$, UVB=12 mW/cm$^2$) complete cross-linking of the mass (the extractable proportion, i.e., the proportion not crosslinked, is less than 5% by weight) was achieved. A transparent product insoluble in organic solvents was obtained.

Example 26

The procedure of Example 9 was repeated, except that 5.03 mg ($1,959 \times 10^{-6}$ mol) of Cat 4 were used instead of 32 mg of Cat 1. The mixture contained 100 ppm by weight of platinum, calculated as the element. The total mixture was stable for at least 4 weeks at room temperature and with exclusion of light. After heating for 10 minutes at 100° C., a complete cross-linking of the mass (the extractable proportion, i.e., the proportion not cross-linked, is less than 5% by weight) was achieved. A clear, brittle mass was obtained.

Example 27

The procedure of Example 9 was repeated, except that 2.9 mg ($1,959 \times 10^{-6}$) of Cat 7 were used instead of 32 mg of Cat 1. The mixture contained 100 ppm by weight of platinum, calculated as element. The total mixture was stable for at least 1 week at room temperature and with exclusion of light. After heating for 8 minutes at 80° C., a complete cross-linking of the mass (the extractable proportion, i.e., the proportion not cross-linked, is less than 5% by weight) was achieved. A clear, brittle mass was obtained.

What is claimed is:

1. An organosiloxane which comprises at least one chemically bonded transition metal complex of Pt, Pd, Rh, Ru, Os or Ir having a triazene, tetrazene, tetrazdiene, pentazdiene or triazene oxide ligand.

2. An organosiloxane as claimed in claim 1, comprising at least two units of the formula $$B_m R_n SiO_{\frac{4-n-m}{2}}, \quad (1)$$

in which
B is a radical of the formula $$MX_a Y_b Z_c \quad (2),$$

where
M is Pt, Pd, Rh, Ru, Os or Ir,
X is a triazene, tetrazene, tetrazdiene, pentazdiene or triazene oxide ligand selected from the group consisting of ANNNR$^1$, ANNNR$^1$R$^2$, ANNNA$^1$, ANR²NNNR³A¹, ANNNNA¹) ANNNR⁴NNA¹, ANNNNNA¹ and ANNNOR¹, where R is a monovalent, substituted or unsubstituted hydrocarbon radical having from 1 to 18 carbon atoms per radical, R¹ is a monovalent, substituted or unsubstituted hydrocarbon radical having from 1 to 18 carbon atoms per radical or a radical of the formula —SiR⁵$_d$(OR⁵)$_{3-d}$, R², R³ and R⁴ are identical or different and are a hydrogen atom or a monovalent, substituted or unsubstituted hydrocarbon radical having from 1 to 18 carbon atoms per radical, and A and A¹ are identical or different and are a radical of the formula

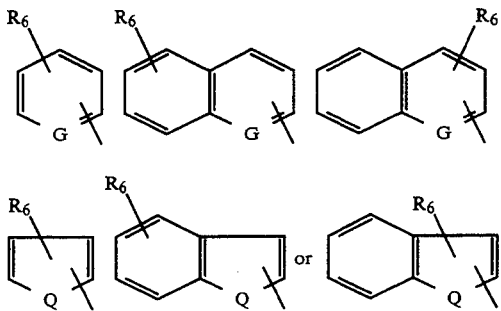

where

G is CH or N and

Q is S, O or NH,

R⁶ is a monovalent, substituted or unsubstituted hydrocarbon radical having from 1 to 12 carbon atoms per radical, or a radical of the formula —F, —Cl, —Br, —I, —H, —NH₂, —NR⁶₂, —NO₂, —OH, —OR⁵, —SH, —CN, —COOH, —COCl, —CONH₂, —COR⁵, —CHO, —SO₂NHR⁵, —SO₃H, —SO₂Cl or —R⁷—SiR⁵$_d$(OR⁵)$_{3-d}$, R⁵ is identical or different and is an alkyl radical having from 1 to 8 carbon atoms per radical and R⁷ is a divalent hydrocarbon radical having from 1 to 8 carbon atoms per radical, d is 0, 1, 2 or 3, Y is identical or different and is a ligand selected from the group consisting of Cl, Br, I, NH₃, PR₃, H, CO, 1,5-cyclooctadiene, pyridine, bipyridine, acetate, acetylacetonate, phenyl cyanide, ethylenediamine, acetonitrile, 2,5-norbornadiene, nitrate, nitrite, H₂O, benzene, diphenylphosphinoethane and 1,3-divinyl-1,1,3,3-tetramethyldisiloxane, Z is identical or different and is a ligand radical selected from the group consisting of Sp—NH₂, Sp—NR¹⁰₂, Sp—NR¹⁰(R⁷)NR¹⁰₂, Sp-4-pyridine, Sp-2-bipyridine, Sp-4-bipyridine, Sp—PR¹⁰(R⁷)PR¹⁰₂, Sp—PR¹⁰₂, Sp—POR¹⁰₂, Sp—P(OR¹⁰)₂, Sp—SH and Sp—SR¹⁰, R¹⁰ is a hydrogen atom or an alkyl radical having from 1 to 6 carbon atoms, Sp is a divalent, SiC-bonded, substituted or unsubstituted hydrocarbon radical having from 1 to 18 carbon atoms per radical, a is 1, 2, 3 or 4, b is 0 or an integer from 1 to 4, c is 1, 2, 3 or 4 and m and n are idential or different and are 0 or an integer from 1 to 3.

3. An organosiloxane as claimed in claim 1, comprising at least two units of the formula $$B'_mR_nSiO_{\frac{4-n-m}{2}}, \quad (3)$$

in which

B' is a radical of the formula $$MX'_eY_f \quad (4),$$

where

X' is a triazene, tetrazene, pentazdiene or triazene oxide ligand radical selected from the group consisting of ANNNSp, ANNNSpR², ANNSpNA¹, ANSpNNNR³A¹, ANNNSpNNA¹ and ANNNOSp, e is 1, 2, 3 or 4, f is 0 or an integer from 1 to 6 and R, M, Y, Sp, R¹, R², R³, R⁴, R⁵, R⁶, R⁷, A, A¹, d, m and n are as defined above.

4. A process for preparing an organsiloxane as claimed in claim 2, wherein an organosiloxane which comprises at least one transition metal complex of Pt, Pd, Rh, Ru, Os or Ir, bonded via ligands, and contains at least two units of the formula $$G_mR_nSiO_{\frac{4-n-m}{2}}, \quad (5)$$

in which

G is a radical of the formula $$MY_gZ_c \quad (6),$$

where n, m, R, M, Y, Z and c are as defined above and g is an integer from 1 to 8, is reacted in the presence of a base with triazene, tetrazene, pentazdiene or triazene oxide compounds selected from the group consisting of ANNNHR¹, ANNNHR², ANNNHA¹, ANHNNNHA¹, ANNNHNNA¹ and ANNNOHR¹, or in the absence of base with triazene, tetrazene, tetrazdiene, pentazdiene or triazene oxide compounds selected from the group consisting of ANNNR¹R², ANNNR¹R²ANNNR¹A¹, ANR²NNNR³A¹ and ANNNR⁴NNA¹ where R¹, R², R³, R⁴, A and A¹ are as defined above.

5. A process for preparing an organosiloxane of formula 3 wherein an organosiloxane which comprises at least one triazene, tetrazene, pentazdiene or triazene oxide radical and contains at least two units of the formula $$X''_mR_nSiO_{\frac{4-n-m}{2}}, \quad (7)$$

in which

X'' is a triazene, tetrazene or triazene oxide radical selected from the group consisting of ANNNHSp, ANHNNNSpA¹ and ANNNOHSp, is reacted in the presence of a base with a transition metal halide complex of the formula $$MY_hHal_i \quad (8),$$

or

X" is a triazene, tetrazene, pentazdiene or triazene oxide radical selected from the group consisting of ANNNRSp, ANNSpNa, ANSpNNNR³A¹, and ANNNSpNNA¹, in the absence of base with a transition metal complex of the formula $$MY_j \quad (9),$$

where
A, A¹, Sp, R M Y m and n are as defined above,
Hal is a chlorine, bromine or iodine atom,
h is 1, 2, 3 or 4,
i is 0 of an integer from 1 to 6 and
j is an integer from 1 to 8.

6. A cross-linkable organopolysiloxane composition comprising
(A) organopolysiloxanes which comprises radicals having aliphatic carbon-carbon multiple bonds, and
(B) organopolysiloxanes having Si-bonded hydrogen atoms, or
(C) organopolysiloxanes which comprise radicals having aliphatic carbon-carbon multiple bonds and Si-bonded hydrogen atoms, and
(D) catalysts, comprising at least one chemically bonded transition metal complex of Pt, Pd, Rh, Ru, Os or Ir having a triazene, tetrazene, tetraziene, pentazdiene or triazene oxide ligand.

* * * * *

UNITED STATES PATENT AND TRADEMARK OFFICE
CERTIFICATE OF CORRECTION

PATENT NO. : 5,426,200
DATED : June 20, 1995
INVENTOR(S) : ORGANOSILOXANE-BONDED TRANSITION METAL COMPLEXES It is certified that error appears in the above-identified patent and that said Letters Patent is hereby corrected as shown below:

Column 2, line 52, should end with "divinyl-1,1,3,3-tetramethyldisiloxane".

Line 53, should begin by inserting --- Z --- prior to "is identical".

Signed and Sealed this

Twenty-eighth Day of May, 1996

Attest:

BRUCE LEHMAN

*Attesting Officer*        *Commissioner of Patents and Trademarks*